(12) United States Patent
Tachibana

(10) Patent No.: US 7,264,148 B2
(45) Date of Patent: Sep. 4, 2007

(54) DRUG CONTAINER AND DRUG INFUSION DEVICE COMPRISING THE SAME

(75) Inventor: Yasuharu Tachibana, Fuji (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 223 days.

(21) Appl. No.: 10/489,334

(22) PCT Filed: Sep. 11, 2002

(86) PCT No.: PCT/JP02/09257

§ 371 (c)(1),
(2), (4) Date: Sep. 17, 2004

(87) PCT Pub. No.: WO03/024385

PCT Pub. Date: Mar. 27, 2003

(65) Prior Publication Data

US 2005/0029277 A1    Feb. 10, 2005

(30) Foreign Application Priority Data

Sep. 12, 2001  (JP) ............................. 2001-276723

(51) Int. Cl.
*G06F 17/00*    (2006.01)
(52) U.S. Cl. .................... 235/375; 705/3; 128/200.14; 128/200.21; 128/203.27
(58) Field of Classification Search ................ 235/375; 705/3; 128/200.14, 200.21, 203.27
See application file for complete search history.

(56) References Cited

U.S. PATENT DOCUMENTS

| 4,978,335 | A | | 12/1990 | Arthur, III | |
|---|---|---|---|---|---|
| 5,681,285 | A | | 10/1997 | Ford et al. | |
| 5,961,641 | A | * | 10/1999 | Hasegawa et al. | 713/1 |
| 2001/0021313 | A1 | * | 9/2001 | Maehara | 399/12 |
| 2004/0065321 | A1 | * | 4/2004 | Stenzler | 128/200.14 |
| 2005/0101905 | A1 | * | 5/2005 | Merry | 604/19 |
| 2006/0218015 | A1 | * | 9/2006 | Walker et al. | 705/3 |

FOREIGN PATENT DOCUMENTS

| JP | 5-500917 | 2/1993 |
|---|---|---|
| JP | 7-502678 | 3/1995 |
| JP | 8-150191 A | 6/1996 |
| JP | 8-509402 | 10/1996 |
| JP | 8-333009 A | 12/1996 |
| JP | 10-507937 | 8/1998 |

(Continued)

*Primary Examiner*—Michael G. Lee
*Assistant Examiner*—Allyson N Trail
(74) *Attorney, Agent, or Firm*—Buchanan Ingersoll & Rooney PC

(57) ABSTRACT

When using a drug container having an identification tag fixed or detachably provided at a predetermined position of the container, the tag having drug data on a kind and a concentration of a drug and both or one of upper and lower limits of a flow rate on a continuous infusion and the upper and lower limits, time and flow rate on a one-shot administration recorded thereon, it is possible to ensure safety by prompting for a stop of injection by a warning when a setting beyond the upper and lower limits is performed and rewrite a liquid infusing time and a flow rate and so on required to be set according to symptoms of a patient.

6 Claims, 10 Drawing Sheets

FOREIGN PATENT DOCUMENTS

| | | |
|---|---|---|
| JP | 11-19210 A | 1/1999 |
| JP | 11-259583 A | 9/1999 |
| JP | 2001-134151 A | 5/2001 |
| JP | 2002-109070 | 4/2002 |
| JP | 2002-172150 | 6/2002 |
| WO | 91/04759 | 4/1991 |
| WO | 94/08647 | 4/1994 |
| WO | 94/25089 | 11/1994 |
| WO | WO 96/36389 A | 11/1996 |
| WO | WO 99/10029 A | 3/1999 |
| WO | WO 99/65548 A | 12/1999 |
| WO | WO 01/56635 A | 8/2001 |
| WO | WO 01/62322 A | 8/2001 |

\* cited by examiner

DRUG CONTAINER AND DRUG INFUSION DEVICE COMPRISING THE SAME

TECHNICAL FIELD

The present invention relates to a drug container and a drug infusion device comprising the same.

BACKGROUND ART

There is a technology of the past as disclosed in National Publication of International Patent Application No. 5-500917 for instance, wherein a syringe body has a barcode fixed thereon as identification means having recorded drug (medicine) data on a drug accommodated in a syringe as a drug container, and the barcode is read on mounting the syringe on a syringe pump so as to easily prepare for administration. National Publication of International Patent Application No. 7-502678 discloses a technology which allows a setting in a permitted range on modification of a dose setting by a user and communicates data on a drug library to the syringe pump from an externally connected system. Furthermore, National Publication of International Patent Application No. 8-509402 discloses the syringe pump wherein an identification tag is provided to a flange portion of the syringe and the identification tag is electrically or magnetically read so as to infuse a liquid based on the read drug or medicine data.

DISCLOSURE OF INVENTION

According to the disclosures, however, there is no mention of upper and lower limits of a flow rate on continuous infusion and the upper and lower limits, time and flow rate on one-shot administration decided by a kind and a concentration of a drug, and data on the upper and lower limits, time and flow rate on the one-shot administration. In particular, there is no mention of prompting a user to stop infusion by a warning when a setting beyond the upper and lower limits is performed by the user.

According to the disclosures, a syringe has an identification tag having stored or recorded drug data on the drug accommodated in the syringe in advance fixed thereon so that the drug data on the identification tag is automatically read on setting the syringe on a pump so as to infuse a liquid based on the drug or medicine data.

For instance, in the case of infusing a larger amount of liquid of drug to a seriously ill patient in a short time, it is necessary to rewrite drug or medicine data on the identification tag. As for an infant or a child, it is necessary to infuse a small amount of liquid of drug for the duration of a long time.

However, a syringe pump of the prior art has only a function of reading the identification tag so that there are the cases where the function is inconvenient because the identification tag cannot be rewritten. And if the function of reading the identification tag is deactivated, there are the cases where all the data on the drug data is erased.

Therefore, the present invention has been implemented in consideration of the problem, and an object thereof is to provide a drug container and a drug infusion device comprising the same, the drug container capable of securing safety by prompting the user to stop infusion by the warning when the setting beyond the upper and lower limits is performed in the case of using the drug container having the identification tag fixed or detachably provided at a predetermined position of the container or syringe, the tag having the kind and concentration of the drug and the drug data of either the upper and lower limits of the flow rate on the continuous infusion or the upper and lower limits, time and flow rate on the one-shot administration recorded thereon, and also capable of rewriting the drug data on the identification tag.

To solve the problem and attain the object, the present invention is the drug container having the identification tag fixed or detachably provided at the predetermined position of the container, the tag having the data including the data on the drug accommodated or to be accommodated and so on recorded (stored) thereon, the container characterized in that the identification tag comprises a first storage portion (first storage area) in which the drug data on health care and so on not rewritable by health workers is recorded (stored) and a second storage portion (second storage area) in which the drug data on the health care and so on rewritable by the health workers is recorded (stored).

It is also the drug container having the identification tag fixed or detachably provided at the predetermined position of the container, the tag having the data including the data on the drug accommodated or to be accommodated and so on recorded (stored) thereon, the container characterized in that the identification tag comprises the first storage portion in which non-rewritable drug data including the kind and concentration of the drug, the upper and lower limits of the flow rate on the continuous infusion and the upper and lower limits on the one-shot administration is recorded and the second storage portion in which the rewritable drug data including the data on a liquid infusing time, (a drug infusion time) a liquid infusing flow rate (a drug infusion flow rate) and so on is recorded.

The identification tag is characterized by being a magnetic chip for performing magnetic reading and rewriting or an integrated circuit chip for performing the reading and rewriting by driving a circuit by means of power generation through electromagnetic induction with a wave received by an antenna.

The container is the syringe for infusing the liquid of drug charged in advance by movement of a pusher, and is characterized in that the identification tag is fixed on a flange portion or a syringe body.

It is also the drug infusion device comprising the drug container, characterized by comprising loading means for rendering the container detachably loadable and infusing the liquid, reading and rewriting means for reading and rewriting the drug data recorded on the identification tag after being loaded on the loading means, display means for displaying the read drug data, infusion setting means for having both or one of the upper and lower limits of the flow rate on the continuous infusion and the upper and lower limits, time and flow rate on the one-shot administration set by the user, warning means for giving the warnings including a beep, a display and a vibration, and control means, connected to each of the means, for operating the warning means when the setting by the infusion setting means is outside a range of the read drug data.

It is also the drug infusion device comprising the drug container, characterized by comprising the reading and rewriting means for loading the container detachably and reading and rewriting the drug data recorded on the identification tag after the loading, and connection means for connecting the reading and rewriting means to an external apparatus, and performing the reading and rewriting by using the external apparatus.

And the reading and rewriting means is characterized by performing the reading and rewriting in a state of accommodating the container in a sterilized bag.

It is also the drug infusion device comprising the drug container, characterized by comprising syringe loading means for loading the syringe detachably and moving the pusher to infuse the liquid, the reading and rewriting means for reading and rewriting the drug data recorded on the identification tag after the loading on the syringe loading means, the display means for displaying the read drug or medicine data, the infusion setting means for having both or one of the upper and lower limits of the flow rate on the continuous infusion and the upper and lower limits, time and flow rate on the one-shot administration set by the user, the warning means for giving the warnings including a beep, a display and a vibration, and the control means, connected to each of the means, for operating the warning means when the setting by the infusion setting means is outside a range of the read drug data.

It is also the drug infusion device comprising the drug container, characterized by comprising the reading and rewriting means for loading the syringe detachably and reading and rewriting the drug data recorded on the identification tag after the loading, and connection means for connecting the reading and rewriting means to an external apparatus, and performing the reading and rewriting by using the external apparatus.

And the reading and rewriting means is characterized by performing the reading and rewriting in a state of accommodating the syringe in the sterilized bag.

BEST MODE FOR CARRYING OUT THE INVENTION

Hereafter, a description will be given as to an embodiment of the present invention which is the case where a drug container is a syringe and a drug infusion device is applied to a syringe pump. It goes without saying that, other than the syringe pump, the drug infusion device may be a peristaltic-type infusion apparatus, a roller-type infusion apparatus, a diaphragm-type infusion apparatus or the like having an identification tag storing data on drugs for a drug (infusion) bag as the drug container so as to read the contents of the identification tag, and is not limited to a configuration described below.

Figure 1:
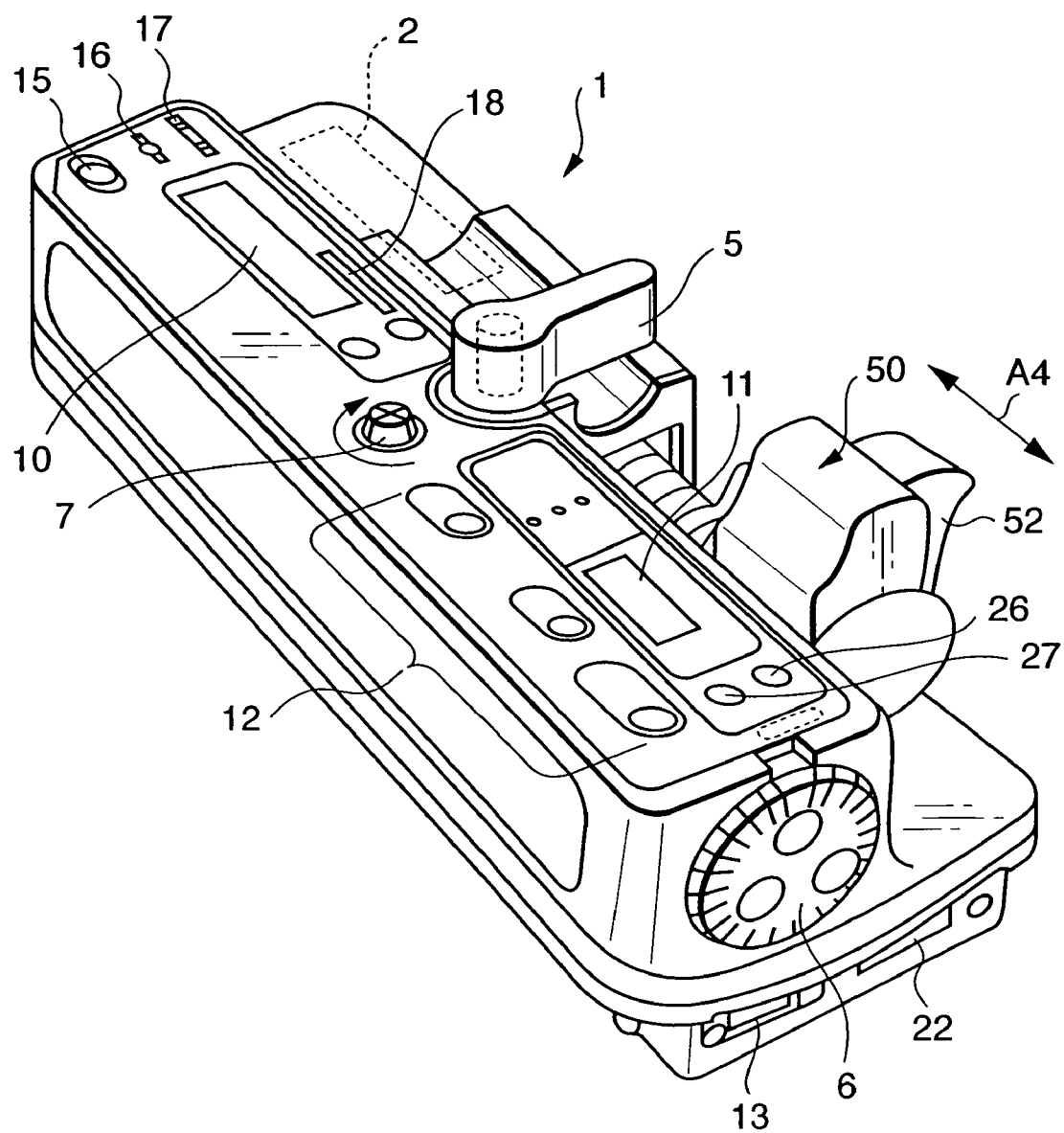
FIG. 1 is an external perspective view of a syringe pump 1.

FIG. 1 is an external perspective view of a syringe pump 1 as an example of the drug infusion device, visibly showing an operation portion 12 as an infusion setting means for setting the flow rate and so on and a setting dial 6 ordinarily operated by a right hand.

In FIG. 1, the syringe pump 1 is a minute amount sustained infusion pump for the purposes of drug solution infusions such as nutritional support, blood transfusion, chemotherapeutic drugs and anesthetics in ICU, CCU and NICU. Its operability is improved by providing a display portion 11 as display means to be adjacent to the operation portion 12 so as to roughly concentrate on a top surface as shown in FIG. 1.

The operation portion 12 and display portion 11 are totally covered with an embossed sheet cover, and have a drip-proof design to satisfy a drip-proof test of JIS (Japanese Industrial Standard) 0920. For instance, they are so highly drip-proof that a carelessly spilt drug solution and so on of the drug can be easily wiped off and inward infiltration thereof can be prevented.

For this reason, its upper and lower covers are integrally formed with a chemical-resistant molding resin material, and mutual bonding faces of the covers are screwed after putting a rubber seal made of silicon elastomer between them in order to prevent a foreign matter such as a liquid from coming in.

To emphasize high precision of the infusion and improvement in the operability, accurate infusion operation control by a microcomputer is implementable, and an operation indicator 7 as warning means is provided by projecting upward at a position easily visible from the outside. The operation indicator 7 lights up, blinks and performs rotative indication in a plurality of colors such as red and green so that its operating state and warning state can be monitored even from a distance and so safety can be fully ensured.

Furthermore, a buzzer is built in so that, when the setting beyond the upper and lower limits is performed by using the operation portion 12 or setting dial 6 in the case of setting one or both of the upper and lower limits of the flow rate on the continuous infusion and the upper and lower limits, time and flow rate on the one-shot administration as will be described later, it prompts the user to stop the infusion by the warning with sound and light in conjunction with the operation indicator 7. Thus, it has a warning function in which the safety is taken into consideration.

It is also small and lightweight, and is designed to be convenient to use and easy to carry even in the case of simultaneously using a plurality thereof. Furthermore, it is possible to set numerical values according to a rotational speed and a rotation direction in a short time by turning the setting dial 6 on a right side of the apparatus. And it is also possible to display a set value in the display portion 11 of a display panel so as to easily change a numerical setting such as the flow rate just by one action of operating the setting dial 6.

Furthermore, it has a shape capable of multiple uses (simultaneous use of many pieces) and an easy-to-use design capable of buildup. Its geometry is a small size of height 110 mm×width 322 mm×depth 115 mm for instance, its weight is 1.6 kg or so, and its power sources are three systems of an AC commercial power, an internal battery and DC12VA.

The internal battery requires charging time of 15 hours, and is covered with a cap and detachably provided by making a connector connection at a bottom of the lower cover so as to be easily replaceable from the outside. Its replacement life is three years or longer, and its charge control is trickle charge. Furthermore, over discharge and charge are prevented by cell breakage detection and cell breakage safety measures of a charge battery. And a heat-resistant (Ni—Cd) battery is used so that a brand new battery can operate for 120 minutes or longer until a warning occurrence and 150 minutes or longer until a shutdown.

In addition, a display portion 10 for gamma infusion, display portions 11 for the flow rate, planned amount and summed amount and so on are provided on an operation panel while the setting dial 6 is easily detachable for cleaning.

Next, syringe mounting means for setting a syringe 2 at the position indicated in the broken line as an example of the drug container is comprised of a syringe stage of the upper cover, a slit portion for setting the flange portion integrally formed with the syringe body, a clamp support (indicated in the broken line) for rotatively supporting a clamp 5 shown in the drawing, and a slider assembly 50 for setting the pusher of the syringe.

And the slider assembly 50 to be driven in a direction of an arrow A4 in the drawing is linked and fixed to a slider infuse mechanism at ends of a pipe shaft and an inner clutch shaft described later so as to reciprocate on a concave portion of a case. And it is possible to easily mount or remove the pusher of the syringe by manually operating a clutch lever 52 of the slider assembly 50.

An external communication connector 22 is placed below the setting dial 6 so as to allow an external communication function mentioned later, such as the one by connecting to an external medical monitor to be performed for instance, and it is thereby possible to remotely control occlusion detection and motor driving. In addition, a nurse call connector 13 for a nurse call is placed adjacently to the external communication connector 22 so that an occurrence of an abnormal state can be notified to a nurse by connecting it to a nurse call connection terminal close to a bed on placing it in a hospital. Furthermore, the external communication connector 22 allows a doctor to erase and rewrite an identification tag 3 via a communication line by means of the external communication function so as to cope with rapid deterioration of the patient. To be more specific, as will be described later, the warning is given when the setting of the infusion is performed exceeding the drug or medicine data previously set on the identification tag 3, and the warning can be withdrawn in the event of an emergency.

And a power switch 15, an AC/DC lamp 16 and a battery lamp 17 are collectively placed on a left edge to prevent a malfunction.

On the display portion 10, a syringe display lamp 18 is provided for the sake of, on setting the syringe 2 by using the clamp 5, converting a vertical travel distance of the clamp 5 into an electrical signal and then automatically measuring a syringe diameter to display a capacity of the set syringe of 10 cc (ml), 20 cc (ml), 30 cc (ml) or 50 cc (ml).

The operation indicator 7 is made of a transparent acrylic resin, and lights and blinks a plurality of embedded light-emitting diodes appropriately shining in red and green and scatters light inside it as if rotating in the arrow direction shown in the drawing so as to electronically display an infusion operating state. And it blinks in red with the buzzer in the case where the infusion setting exceeds or drops below an allowable value.

Adjacently to the clamp 5, the display lamps (not shown) are provided for the sake of displaying by change-over in three stages a setting detection pressure by an occlusion detection mechanism provided to the syringe pump. A remaining amount alarm lamp, a battery alarm lamp (not shown) and so on are collectively placed adjacently to these lamps.

The display portions 11 has a "7"-segment LED provided thereon, and has a display changeover switch 26 and a summation clear switch 27 provided on the right side thereof.

Figure 2A:
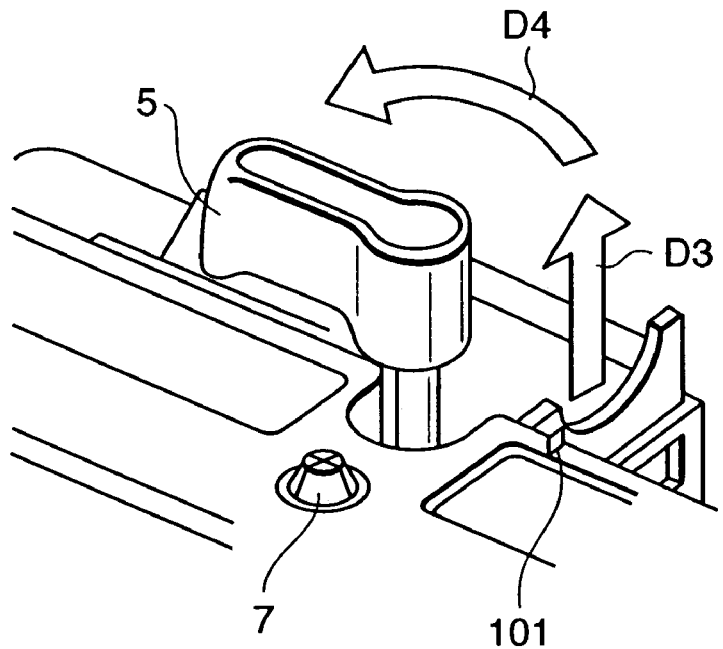
FIG. 2A is a partially enlarged view before setting a syringe.
Figure 2B:
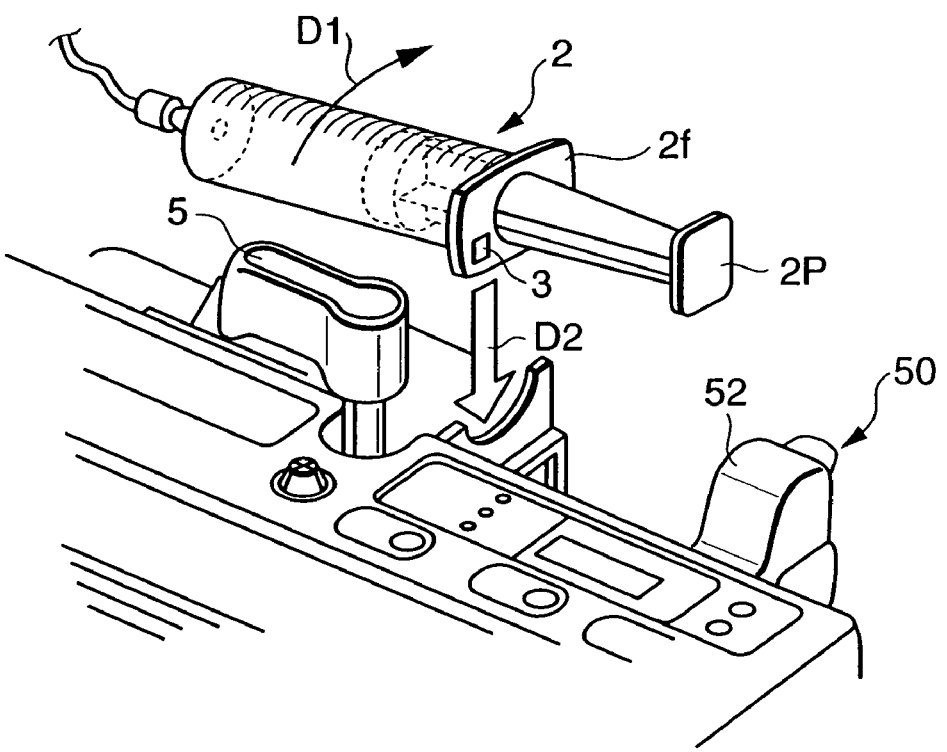
FIG. 2B is a partially enlarged view of an appearance immediately before setting a syringe 2.

In the configuration described above, as shown in the external perspective view of the clamp 5 in FIGS. 2A and 2B, the clamp 5 is raised to an upward arrow D3 and is turned in an arrow D4 direction by approximately 90 degrees in order to set the syringe 2. Thus, the clamp 5 held in a state of being fitted to a vertical projection of the clamp support can remain against an unshown pull strength at an upper end of the clamp support.

A flange portion 2f of the syringe 2 has the identification tag 3 comprised of a magnetic chip as the identification tag, a barcode, a two-dimensional barcode and a rewritable and erasable IC chip fixed thereon. Otherwise, the identification tag 3 has the drug data on the drug accommodated or to be accommodated recorded thereon. To be more precise, the identification tag 3 has the drug data on the kind and concentration of the drug and both or one of the upper and lower limits of the flow rate on the continuous infusion and the upper and lower limits, time and flow rate on the one-shot administration recorded thereon by using a data input apparatus. Here, the syringe having the drug accommodated in advance is referred to as a prefilled syringe.

If the flange portion 2f of the syringe 2 is set on the slit, electrical detection becomes possible by means of a reading portion 101 which is reading means placed at a position corresponding to the identification tag 3. Thereafter, if the syringe 2 is set on the syringe stage and then the clamp 5 is turned to an arrow D1, the locked state is released and it is pulled in an arrow D2 direction in the drawing to clamp the syringe 2 so that the setting of the container portion of the syringe is finished.

Subsequently, a clutch is released to move the slider. At this time, the slider can be manually moved by pushing the clutch lever 52 of the slider assembly 50 shown in FIG. 1.

Thus, if the clutch lever 52 is released after a pusher 2P of the syringe 2 contacts the slider assembly 50, right and left hooks (not shown) automatically holds the pusher 2P of the syringe 2. To be more specific, if the clutch lever 52 is released, the hooks of the slider sandwich the pusher 2P of the syringe 2. Thus, the setting by syringe loading means is finished.

The slider assembly 50 has an unshown slider infuse mechanism provided thereto, where the pusher 2P is pushed to infuse a drug solution and it moves in a direction opposite to an infuse direction on completion of the infusion operation so as to return to its initial position.

Figure 3:
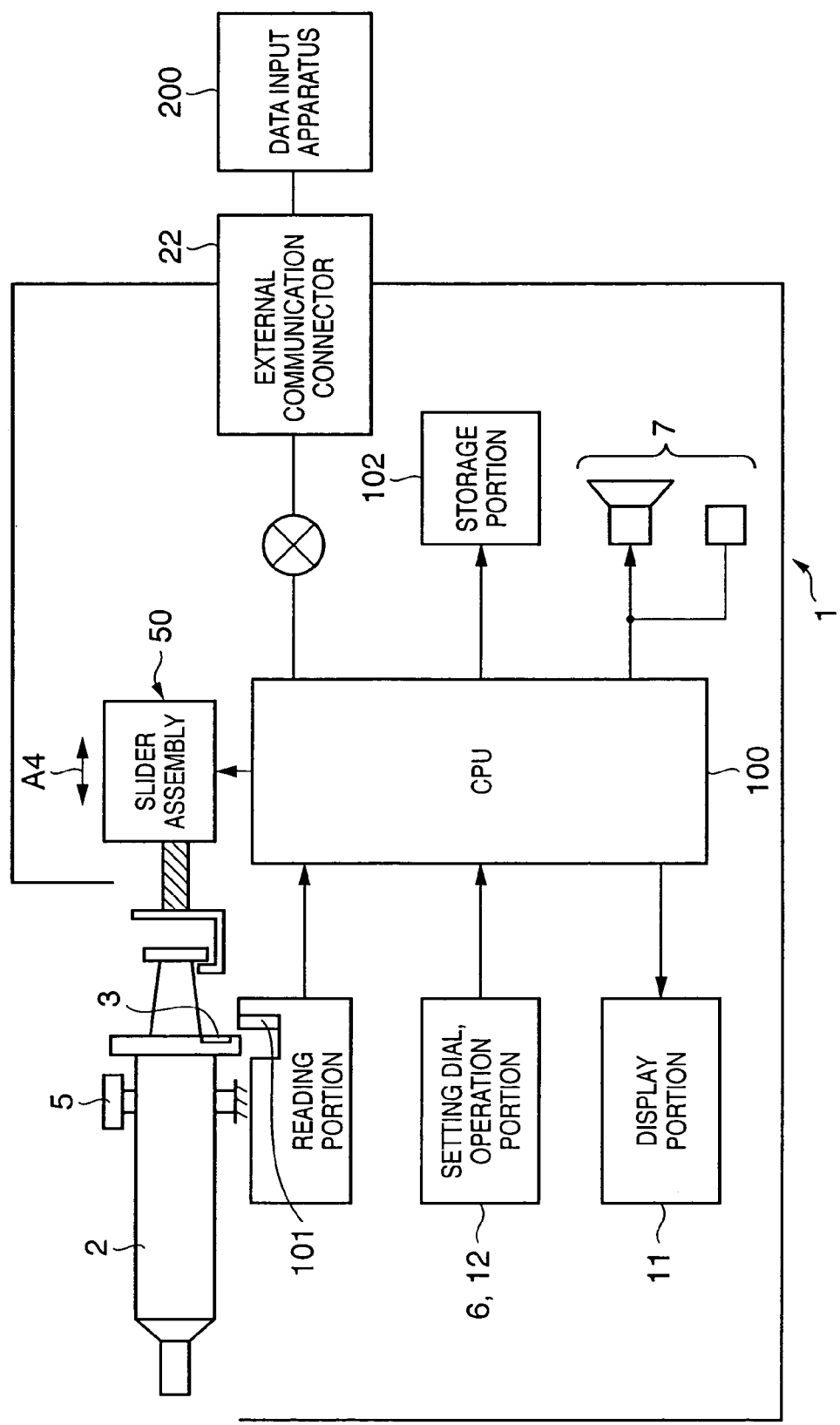
FIG. 3 is a block diagram of the syringe pump 1.

FIG. 3 is a block diagram of the syringe pump 1. In FIG. 3, a CPU 100 as control means has the respective means connected thereto, and the medicine and drug solution are fed under control of the CPU 100. First, a motor driver (not shown) which drives the slider assembly 50 for moving the pusher is connected and moves in the arrow A4 direction. The identification tag 3 fixed on the flange portion is optically and electromagnetically detected as digital data by the reading portion 101 which is the reading means so as to have the drug or medicine data read and stored in a storage portion 102. The operation portion 12 and setting dial 6 as the infusion setting means are connected to display setting results in the display portion 11. The operation indicator 7 and buzzer as the warning means are connected to call attention when a wrong setting is performed as mentioned later. The external communication connector 22 allows the external medical monitor or the data input apparatus 200 to be connected thereto so as to perform the external communication function and thereby remotely control the occlusion detection and motor driving.

Figure 4:
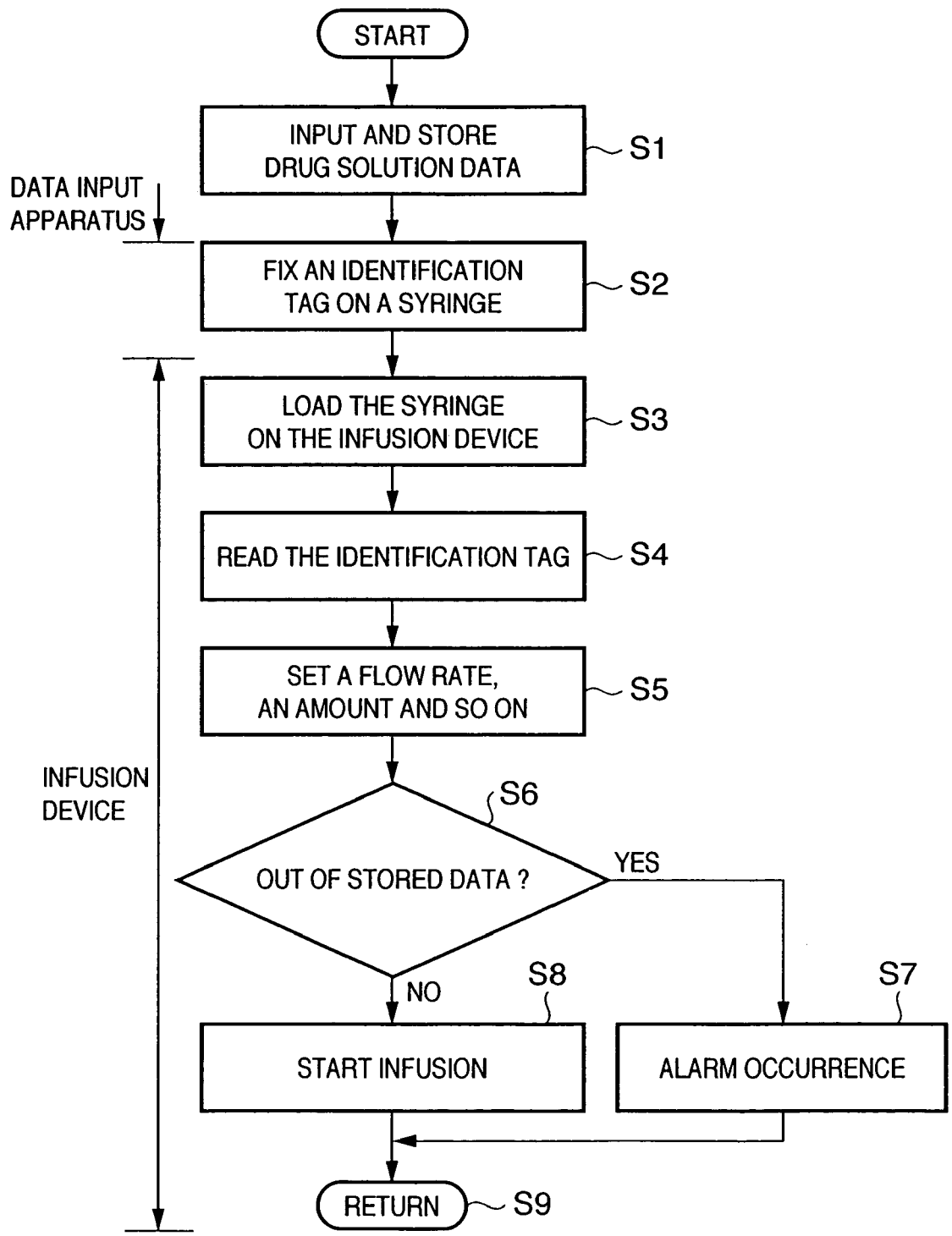
FIG. 4 is an operation flowchart of the syringe pump.

FIG. 4 is a flowchart showing an operation example of the syringe pump of the above configuration. Referring to this diagram, in a step S1 first, the drug data on the drug accommodated or to be accommodated in the syringe 2 is recorded on the identification tag 3 as identification means by using the data input apparatus and stored thereon. At this time, in the case where the identification tag 3 is not fixed on the flange portion 2*f* of the syringe 2 in advance, it is fixed thereon in a step S2. To record the infusion data on the kind and concentration of the infusion and both or one of the upper and lower limits of the flow rate on the continuous infusion and the upper and lower limits, time and flow rate on the one-shot administration, the identification tag 3 uses one of the magnetic chip, barcode, two-dimensional barcode and rewritable and erasable IC chip, and the reading portion 101 is modified accordingly.

Subsequently, in a step S3, the syringe 2 is set as shown in FIG. 2. If it is detected that the clamp has been moved to a set position, it moves on to a step S4, so that the identification tag 3 is read by the reading portion 101 and read data is stored in the storage portion 102. Subsequently, the patient or the nurse performs the setting of one of the upper and lower limits of the flow rate on the continuous infusion and the upper and lower limits, time and flow rate on the one-shot administration by operating the operation portion 12 and setting dial 6.

Next, it moves on to a step S6 to compare the set value set in a step S5 to the value stored in the storage portion 102. And if it is determined to be out of the stored data, it moves on to a step S7 to prompt for a change in the setting with the operation indicator 7 and buzzer, and returns in a step S9 to wait for resetting.

As a result of the comparison to the value stored in the storage portion 102 in the step S6, if it is determined to be within the stored data, it moves on to a step S8 to start the infusion and then returns in the step S9.

If the infusion of liquid is finished as above, automatic erasure and rewriting are performed to render the syringe incapable of reuse in the case where the identification tag 3 is the erasable and rewritable IC chip for instance.

As described above, in the case of using the identification tag having recorded the drug data on the kind and concentration of the drug and both or one of the upper and lower limits of the flow rate on the continuous infusion and the upper and lower limits, time and flow rate on the one-shot administration by having the tag fixed or detachably provided at the predetermined position of the syringe 2 as the container, it is possible to ensure the safety by prompting for a stop of the infusion when the setting out of the upper and lower limits is performed by the user.

Figure 5A:
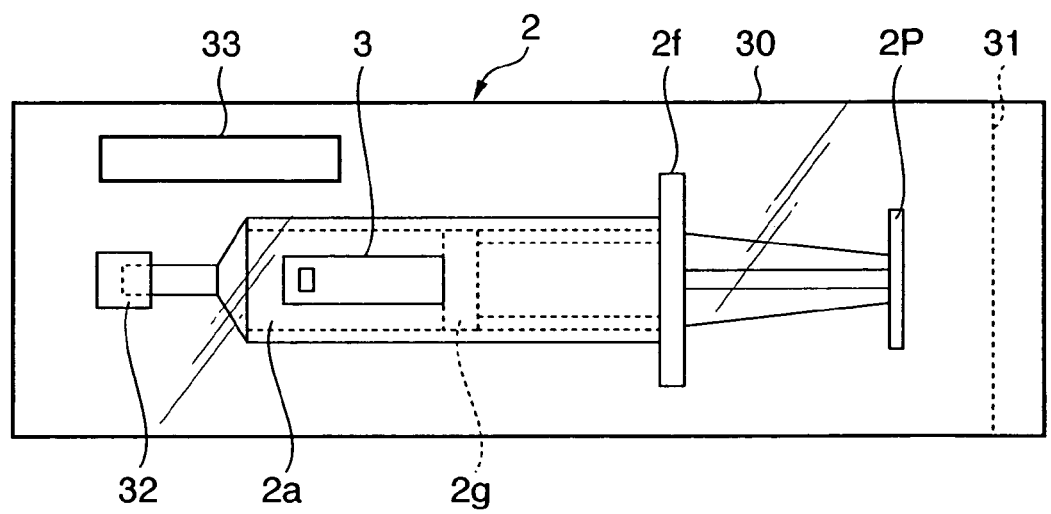
FIG. 5A is an external view of the syringe according to a second embodiment.
Figure 5B:
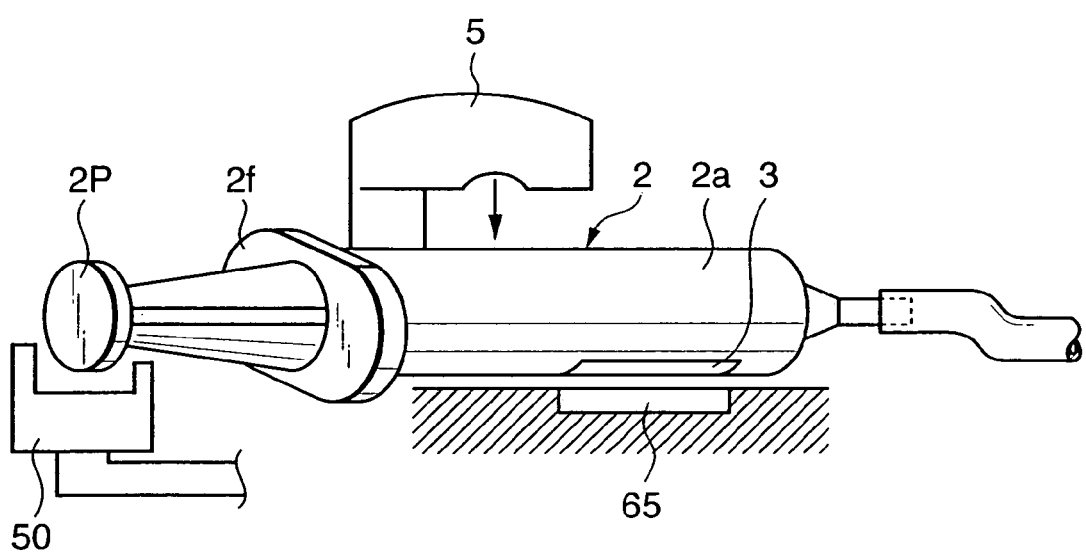
FIG. 5B is an external perspective view showing a relevant part after loading the syringe 2 on the syringe pump 1.

Next, FIG. 5A is an external view of the syringe 2 as an example of the drug container according to a second embodiment. FIG. 5B is an external perspective view showing a relevant part after loading the syringe 2 on the syringe pump 1. In FIGS. 5A and 5B, a description will be omitted by giving the same symbols as to components already described.

First, in FIG. 5A, the syringe 2 is the prefilled syringe which is filled with a predetermined drug and sterilized in advance, and has a cap 32 for maintaining sterility provided to a delivery outlet so that the sterility is maintained by workings with a gasket 2*g*. The syringe 2 has the identification tag 3 fixed on a side 2*a* of its body by adhesion and so on, but the tag 3 may also be provided to either the flange portion 2*f* or the pusher 2P as with the preceding embodiment.

As shown in the drawings, the identification tag 3 is the tag wherein the IC chip connected to a loop antenna is specially printed on a base. And it does not have the power source itself but generates electric power by electromagnetic induction with a wave received by the loop antenna so as to drive a circuit by means of the power generation and thereby perform the reading and rewriting. As a representative example of use, a commuter pass for an automatic ticket gate of JR already put into practical use will be taken up. While the identification tag 3 has the drug data on the kind and concentration of the drug and both or one of the upper and lower limits of the flow rate on the continuous infusion and the upper and lower limits, time and flow rate on the one-shot administration and so on stored thereon, the data on the time and flow rate, patients and health workers (one's doctor, nurse, pharmacist and so on) is rewritable, for instance.

The syringe 2 thus prepared is sealed and delivered to a hospital and so on by a pharmaceutical manufacturer and so on after setting it in transparent or light-transmitting storage bag 30 having a drug label 33 recorded at an easy-to-see location. The nurse takes out the syringe 2 inside the bag thus provided by tearing it along a perforation 31, and loads it on the syringe pump by using the above-mentioned procedure so that the identification tag 3 faces downward as shown in FIG. 5B. Consequently, the identification tag 3 stops at a position close to and opposed to a reading and rewriting portion 65 built in the syringe pump so as to be ready for the reading and rewriting.

Figure 6:
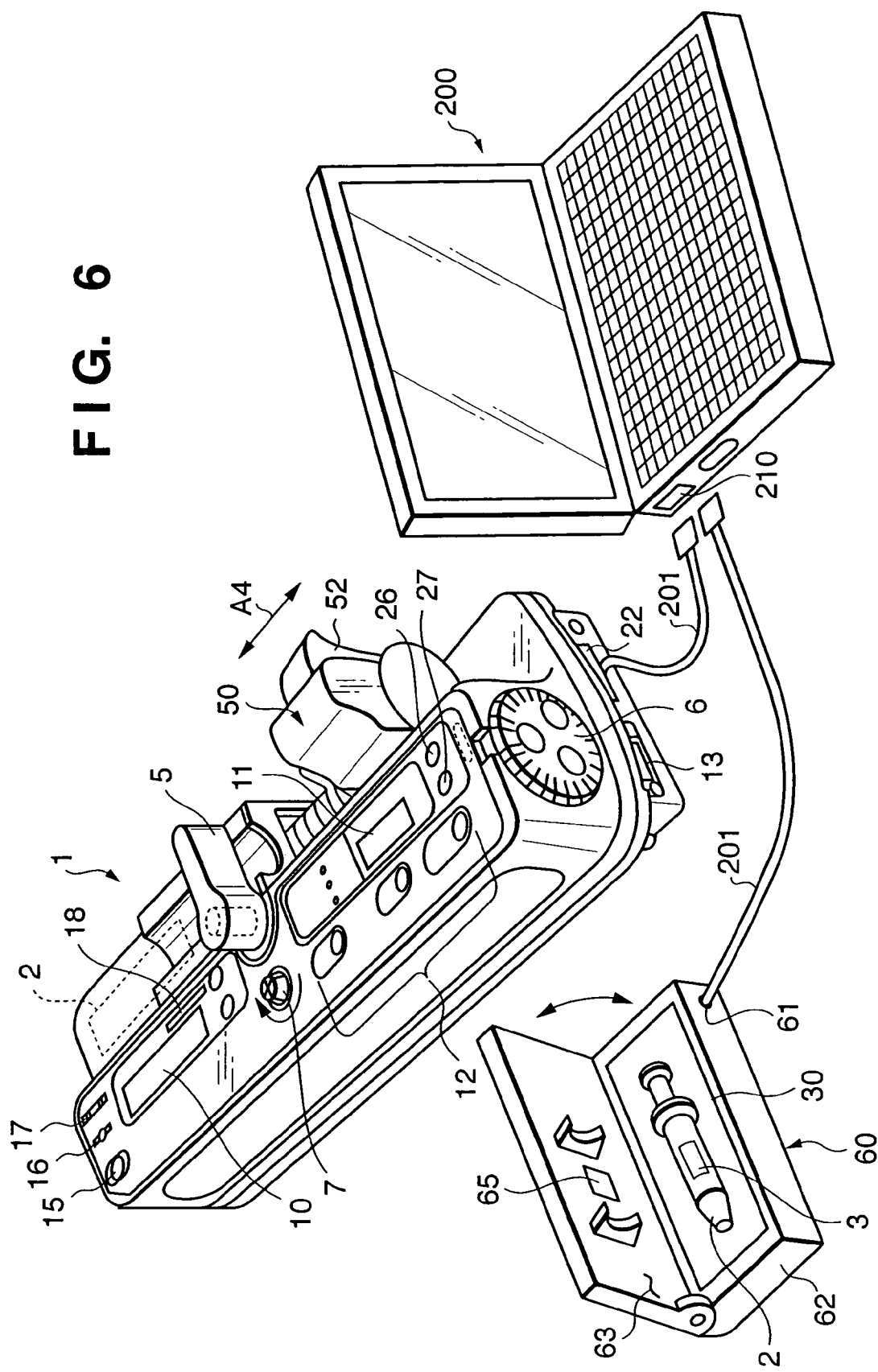
FIG. 6 is an external perspective view showing the syringe pump 1, a data input apparatus 200 and a dedicated apparatus 60 for reading and rewriting.

FIG. 6 is an external perspective view showing the syringe pump 1, data input apparatus 200 and a dedicated apparatus 60 for the reading and rewriting. In FIG. 6, a connection cable 201 is connected between the external communication connector 22 of the syringe pump 1 and an external connector 210 of the data input apparatus 200 which is a notebook PC for instance. And after loading the syringe 2 as shown in FIG. 5B, the doctor performs the reading of the drug data on the identification tag 3 and the reading and rewriting of the data on the time and flow rate, patients and health workers (one's doctor, nurse, pharmacist and so on) and so on.

Otherwise, a specific health worker such as the doctor performs the reading of the drug or medicine data on the identification tag 3 and the reading and rewriting of the data on the time and flow rate, patients and health workers (one's doctor, nurse, pharmacist and so on) and so on after connecting the connection cable 201 between an external communication connector 61 of the dedicated apparatus 60 and the external connector 210 of the data input apparatus 200 and loading the syringe 2 in a state of being put in the storage bag 30 as shown in the drawing. To be more specific, the dedicated apparatus 60 is the apparatus dedicated to the reading and rewriting of the identification tag 3, and has the reading and rewriting portion 65 for having the power supplied and operating on connection to the external connector 210 which is a USB connector provided on a cap portion 63. The cap portion 63 is rotatively supported at the edge of a base 62, and is closed after setting it with the identification tag 3 of the syringe 2 facing upward as illustrated so that the identification tag 3 is located at the position close to and opposed to the reading and rewriting portion 65 to be ready for the reading and rewriting as described above.

The dedicated apparatus 60 allows the data on the patients and health workers (one's doctor, nurse, pharmacist and so on) to be read and rewritten in the state of being put in the storage bag 30 and handled only by the specific health worker such as the doctor, so that it can be handed to the nurse to prevent a wrong setting as to a liquid infusing time and the flow rate on the site.

Figure 7:
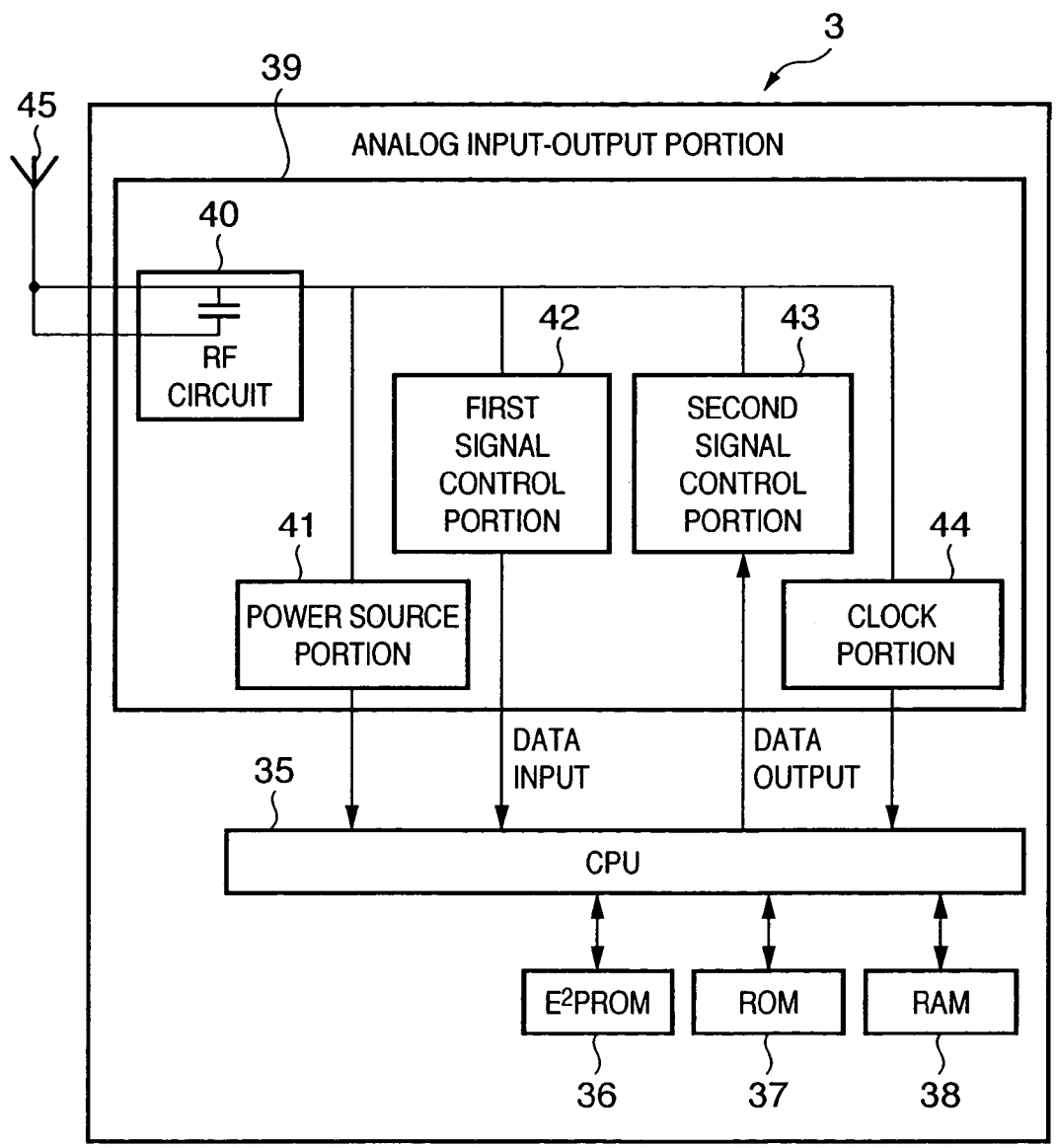
FIG. 7 is a block diagram of an identification tag 3.

FIG. 7 is a block diagram of the identification tag 3. In FIG. 7, the identification tag 3 is comprised of an analog input-output circuit 39 and a control portion (CPU) 35 which is a digital circuit. The analog input-output circuit 39 is connected with a radio frequency circuit (RF circuit) 40 which receives radio transmission of a predetermined frequency transmitted from the reading and rewriting portion 65 by being connected to a loop antenna 45. The radio frequency circuit 40 is connected with a power source portion 41 for supplying a predetermined voltage to the CPU 35, a first signal control portion 42 for converting the read drug data to a digital signal and sending it to the CPU 35, a second signal control portion 43 for converting the digital signal on the time and flow rate sent from the CPU 35 to an analog signal and sending it to the radio frequency circuit 40, and a clock portion 44 for generating a clock signal to start up and drive the CPU 35.

The CPU 35 is connected with a storage area (E2PROM) 36 which is a flash memory and is readable and rewritable by the specific health worker such as the doctor and an ROM 37 and an RAM 38 which are the storage areas non-rewritable by the specific health worker such as the doctor and capable of write setting only by the pharmaceutical and medical appliance manufacturers. As described above, the E2PROM 36 is connected to the dedicated apparatus to rewriting 60 or the syringe pump 1, and stores the liquid infuding time, liquid infuding flow rate and so on which are set by using the data input apparatus 200. The ROM 37 as a non-rewritable first storage portion has drug information such as the drug data on the kind and concentration of the drug and both or one of the upper and lower limits of the flow rate on the continuous infusion and the upper and lower limits, time and flow rate on the one-shot administration and so on written and permanently stored thereon on manufacturing (shipment) thereof by the pharmaceutical and medical appliance manufacturers. The RAM 38 is used as the storage portion on signal processing and so on.

Figure 8:
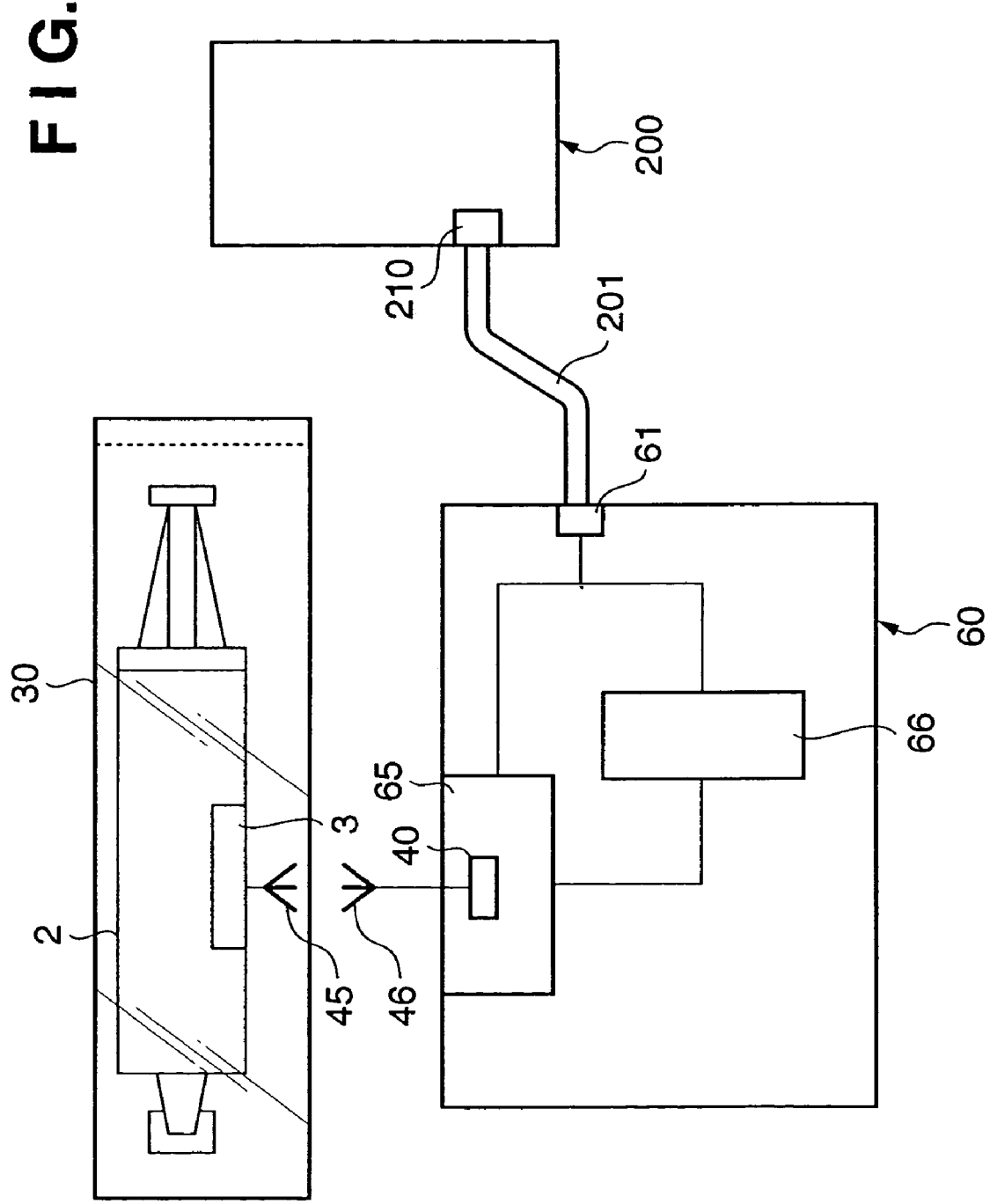
FIG. 8 is a block diagram showing the appearance after loading the syringe 2 in a sterilized bag 30 on the dedicated apparatus 60.

FIG. 8 is a block diagram showing the appearance after loading the syringe 2 in the storage bag 30 on the dedicated apparatus 60. In FIG. 8, omitting a description of the already described components by giving them the same numbers, the loop antenna 45 of the identification tag 3 is set opposite a loop antenna 46 connected to the reading and rewriting portion 65. The reading and rewriting portion 65 has the radio frequency circuit 40 built therein, and reads and rewrites the identification tag 3 by exchanging control signals sent from a signal control portion 66.

Figure 9:
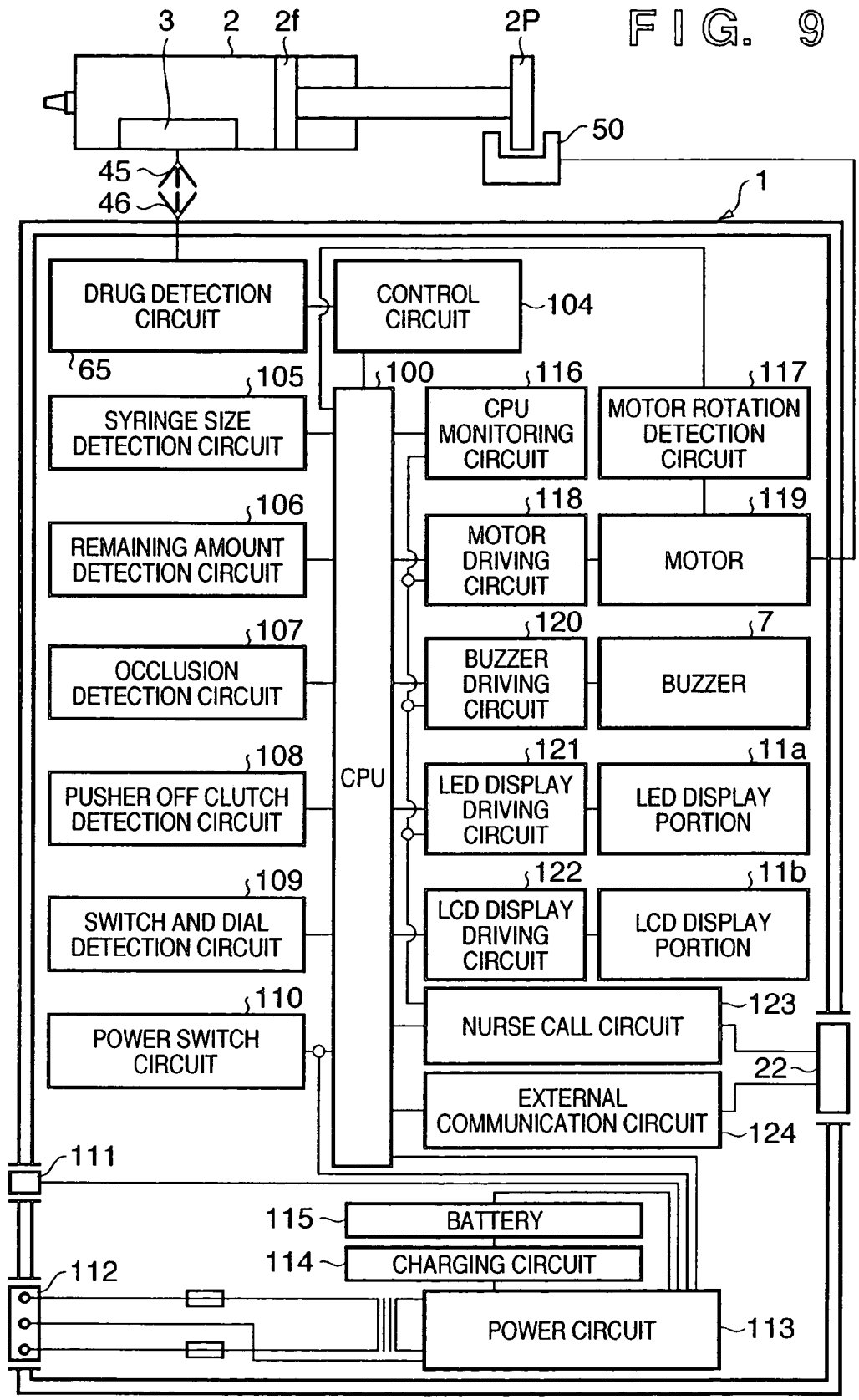
FIG. 9 is a block diagram of the syringe pump 1.

FIG. 9 is a block diagram of the syringe pump 1 as an example of the drug infusion device. In FIG. 9, omitting a description of the already described components by giving them the same numbers, a control circuit 104 is connected to the CPU 100 as the control means. The control circuit 104 is connected to the loop antenna 46 connected to the reading and rewriting portion 65. The loop antenna 46 is placed opposite the loop antenna 45 of the identification tag 3 in the state of having the syringe 2 loaded as an example of the drug infusion device so as to read and rewrite the identification tag 3 by exchanging the control signals sent from the control circuit 104.

The CPU 100 is connected with a syringe size detection circuit 105 for detecting an outside diameter of the syringe 2 by detecting the travel distance of the clamp 5 for the sake of setting the syringe 2, a remaining amount detection circuit 106 for detecting a remaining amount of the drug by detecting the travel distance of the pusher, an occlusion detection circuit 107 for detecting an occlusion state of a tube by detecting an increase in a pusher traveling force, and a pusher off clutch detection circuit 108 for detecting the pusher dropped off the slider assembly 50. The CPU 100 is also connected with a switch and dial detection circuit 109 for detecting the set value set by operation of the switch and dial and sending it to the CPU 100, a power switch circuit 110 for detecting on and off of the power switch, a monitoring circuit 116 for monitoring the operation of the CPU 100, a motor driving circuit 118 for driving a motor 119 which drives the slider assembly 50, and a motor rotation detection circuit for measuring liquid infusing by detecting a rotation amount of the motor 119.

Furthermore, the CPU 100 is connected with a buzzer driving circuit 120 for driving a buzzer 7, an LED display driving circuit 121 for driving an LED display portion 11a, a liquid crystal display driving circuit 122 for driving a liquid crystal portion 11b, a nurse call circuit 123 for calling the nurse in the case of an emergency by being connected to the external communication connector 22, and an external communication circuit 124 for rewriting the identification tag 3 by being connected to the data input apparatus 200 as described above.

A power circuit 113 is connected with a power input connector 112 so that it has the power supplied from the commercial power and drives a charging circuit 114 to charge a charge battery 115 and supply the power to the power switch circuit 110. The power circuit 113 is further connected with a connector 111 for a DC power input so as to allow a drive by a DC power source.

Figure 10:
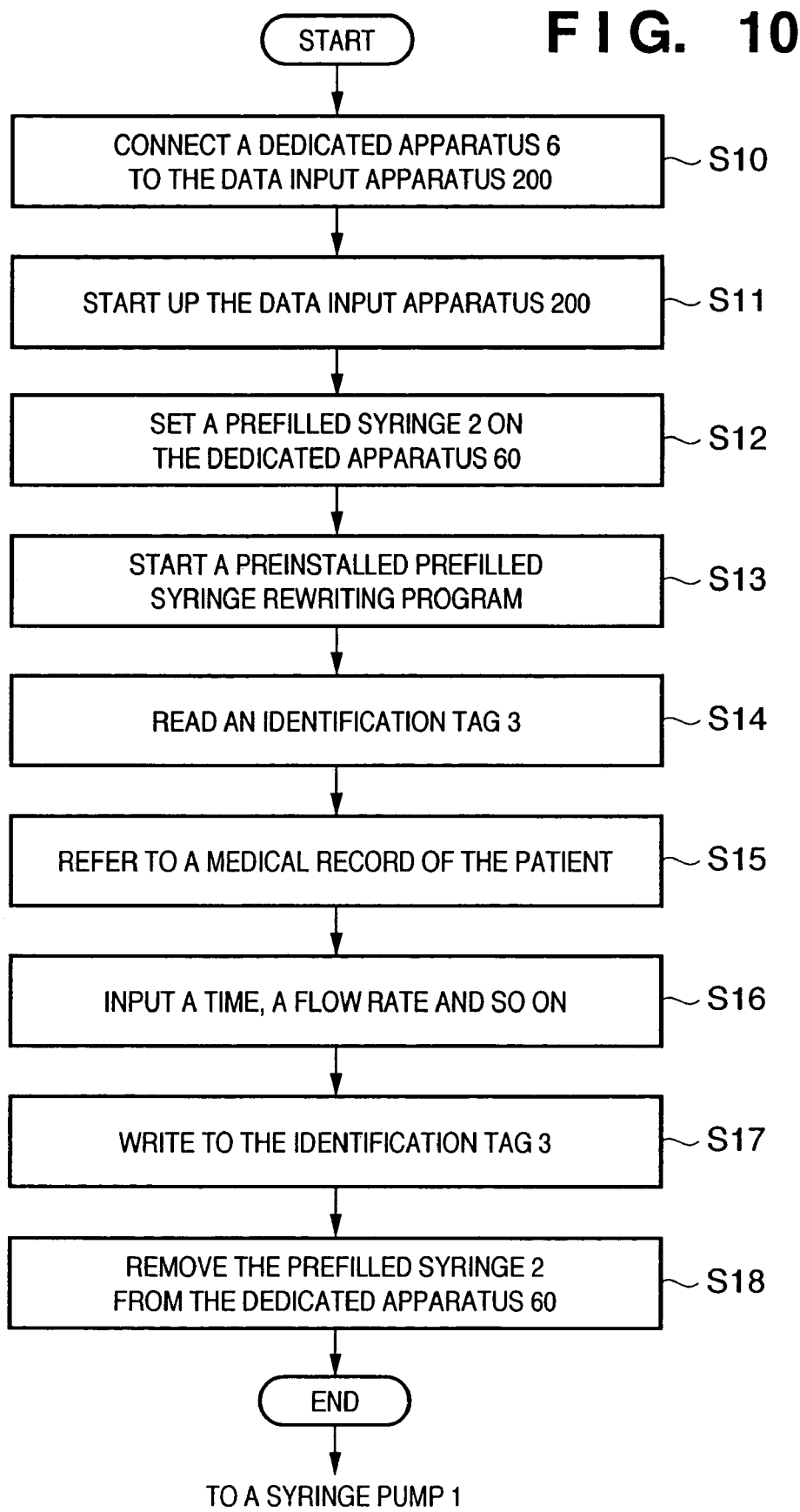
FIG. 10 is a flowchart for describing an operation of loading the syringe 2 in the sterilized bag 30 on the dedicated apparatus 60 and rewriting the identification tag 3.

FIG. 10 is a flowchart for describing the operation of loading the sterilized prefilled syringe 2 storing the drug in advance in the sterilized bag 30 on the dedicated apparatus 60 and rewriting the identification tag 3. In FIG. 10, in a step S10 first, the dedicated apparatus 60 is connected to the data input apparatus 200 as shown in FIG. 8. Subsequently, the data input apparatus 200 is started up in a step S11, and the prefilled syringe 2 in the storage bag 30 is set on the dedicated apparatus 60 in a step S12, and then a preinstalled prefilled syringe rewriting program is started up in a step S13. Then, the identification tag 3 is automatically read in a step S14, and reading results are displayed on the data input apparatus. Consequently, the specific health worker such as the doctor refers to a drug record of the patient to whom the liquid infusing is performed in a step S15, and determines the data such as the liquid infusing time or the liquid infusing flow rate of the drug according to symptoms of the patient and so on, and inputs them together with the data on the patient and health workers (one's doctor, nurse, pharmacist and so on) by using a keyboard of the data input apparatus 200 and so on in a step S16. Consequently, the writing and rewriting are performed to the E2PROM 36 as a second storage portion capable of writing and rewriting the identification tag 3 in a step S17.

Next, in a step S18, the rewriting is finished by removing the prefilled syringe 2 from the dedicated apparatus 60. Thereafter, the specific health worker such as the doctor hands the prefilled syringe 2 in the storage bag 30 to the nurse. The nurse takes the prefilled syringe 2 out of the storage bag 30, and sets it on the syringe pump to perform the liquid infusing to the patient. If the infusion of a predetermined amount of the drug is finished, the data on the patient and health workers (one's doctor, nurse, pharmacist and so on) and prescribed drug data (kinds and infusion amounts, etc. of the drug) are stored as curing (prescription) history in the storage portion. The data on the patient and health workers (one's doctor, nurse, pharmacist and so on) and the prescribed drug data (kinds and infusion amounts, etc. of the drug) are sent to a nurse center, a host computer in the hospital and so on as required via the external communication circuit 124 and the external communication connector 22 so as to be stored and displayed to be checked as required.

In the case of writing and rewriting the identification tag 3 of the syringe 2 set on the syringe pump, the data input apparatus 200 is connected to the external communication connector 22 to rewrite the identification tag 3.

As described above, it is possible to ensure the safety of the identification tag 3 by storing the drug data on the kind and concentration of the drug and both or one of the upper and lower limits of the flow rate on the continuous infusion and the upper and lower limits, time and flow rate on the one-shot administration in the ROM 37 (refer to FIG. 7) and prompting for the stop of the infusion when the wrong setting is performed. As for the liquid infusing time and liquid infusing flow rate required to be set according to the symptoms of the patient, they can be rewritten by storing them in the E2PROM 36 which is the flash memory. Therefore, it is possible to cope with the cases of performing the liquid infusing of a large amount or a small amount of the drug in a short time or performing the liquid infusing of a larger amount or a smaller amount of the drug for a long time.

It also becomes possible, on the host computer and so on, to manage the drug (the prefilled syringe for instance) without a necessity of a major drug database (drug library) so as to prevent a wrong or excessive administration.

The invention claimed is:

1. A drug infusion device comprising:
   a drug container having an identification tag fixed or detachably provided at a predetermined position of the container, the tag having data on a drug accommodated or to be accommodated recorded thereon, wherein the identification tap comprises;
      a first storage portion in which non-rewritable drug data including a kind of the drug and upper and lower limits of a flow rate on a continuous infusion is recorded; and
      a second storage portion in which rewritable data including the data on a liquid infusing time and a liquid infusing flow rate and the data on a patient and health workers is recorded; and
   said drug infusion device further comprising:
      loading means for rendering said container detachably loadable and infusing the liquid;
      reading and rewriting means for reading and rewriting said drug data recorded on said identification tag after being loaded on said loading means;
      display means for displaying said read drug data;
      infusion setting means for having both or one of the upper and lower limits of the flow rate on the continuous infusion and the upper and lower limits, time and flow rate on a one-shot administration set by the user;
      warning means for giving warnings including a beep, a display and a vibration; and
      control means, connected to each of the means, for operating said warning means when a setting by said infusion setting means is outside a range of the read drug data.

2. The drug infusion device according to claim 1, wherein said container is a syringe for infusing the liquid of the drug charged in advance by movement of a pusher, and said identification tag is fixed on a flange portion or a syringe body.

3. The drug infusion device according to claim 1, wherein said reading and rewriting means performs said reading and rewriting in a state of accommodating said container in a sterilized bag.

4. A drug infusion device comprising:
   a drug container having an identification tag fixed or detachably provided at a predetermined position of the container, the tag having data on a drug accommodated or to be accommodated recorded thereon, wherein the identification tap comprises:
      a first storage portion in which non-rewritable drug data including a kind of the drug and upper and lower limits of a flow rate on a continuous infusion is recorded; and
      a second storage portion in which rewritable data including the data on a liquid infusing time and a liquid infusing flow rate and the data on a patient and health workers is recorded;
   wherein said container is a syringe for infusing the liquid of the drug charged in advance by movement of a pusher; and
   said drug infusion device further comprises:
      syringe loading means for loading said syringe detachably and moving said pusher to infuse the liquid;
      reading and rewriting means for reading and rewriting said drug data recorded on said identification tag after the loading on said syringe loading means;
      display means for displaying said read drug data;
      infusion setting means for having both or one of the upper and lower limits of the flow rate on a continuous infusion and upper and lower limits, time and flow rate on a one-shot administration set by a user;
      warning means for giving warnings including a beep, a display and a vibration; and
      control means, connected to each of said means, for operating said warning means when a setting by said infusion setting means is outside a range of read drug data.

5. The drug infusion device according to claim 4, wherein said reading and rewriting means performs said reading and rewriting in a state of accommodating said syringe in a sterilized bag.

6. The drug infusing device according to claim 4, wherein said identification tag is fixed on a flange portion or a syringe body.

* * * * *